(12) United States Patent
Msika

(10) Patent No.: US 8,466,109 B2
(45) Date of Patent: Jun. 18, 2013

(54) COSMETIC METHOD FOR PREVENTING AND/OR TREATING SKIN STRETCHMARKS, AND USE IN DERMATOLOGY

(75) Inventor: Philippe Msika, Paris (FR)

(73) Assignee: Laboratoires Expanscience, Courbevoie (FR)

( * ) Notice: Subject to any disclaimer, the term of this patent is extended or adjusted under 35 U.S.C. 154(b) by 1640 days.

(21) Appl. No.: 10/808,701

(22) Filed: Mar. 25, 2004

(65) Prior Publication Data

US 2004/0180033 A1    Sep. 16, 2004

Related U.S. Application Data

(63) Continuation of application No. 09/806,834, filed as application No. PCT/FR99/02375 on Oct. 5, 1999, now abandoned.

(30) Foreign Application Priority Data

Oct. 5, 1998    (FR) ...................................... 98 12435

(51) Int. Cl.
    *A61K 38/00*    (2006.01)
    *A61K 33/34*    (2006.01)
    *A61K 38/48*    (2006.01)

(52) U.S. Cl.
    USPC ........... 514/18.8; 424/401; 424/641; 424/757

(58) Field of Classification Search
    USPC ....................... 424/757, 641, 401; 514/2, 18.8
    See application file for complete search history.

(56) References Cited

U.S. PATENT DOCUMENTS

| | | | |
|---|---|---|---|
| 4,054,649 A * | 10/1977 | Cariel | ............................ 424/764 |
| 4,584,284 A | 4/1986 | Audhya et al. | |
| 5,444,091 A | 8/1995 | Rapaport et al. | |
| 5,508,033 A | 4/1996 | Briand | |
| 5,614,215 A | 3/1997 | Ribier et al. | |
| 5,719,129 A | 2/1998 | Andary et al. | |
| 5,759,555 A | 6/1998 | Moy | |
| 5,760,079 A | 6/1998 | Shaffer et al. | |
| 5,804,594 A * | 9/1998 | Murad | ............................ 514/474 |
| 6,114,336 A | 9/2000 | Blanc-Ferras et al. | |
| 2001/0014342 A1 | 8/2001 | De La Charriere et al. | |

FOREIGN PATENT DOCUMENTS

| | | | |
|---|---|---|---|
| DE | 4244418 A1 * | 7/1993 | |
| EP | 0 774 249 A2 | 5/1997 | |
| EP | 1 104 672 A1 | 6/2001 | |
| FR | 2 769 502 A1 | 4/1999 | |
| WO | WO-99/38509 | 8/1999 | |
| WO | WO-99/38509 | 9/1999 | |

OTHER PUBLICATIONS

Quelle, G., "Peptide preparation and methods for their manufacture", DE 4244418A1 (Jul. 1, 1993).*

Flick, E., Cosmetic and Toiletry Formulations, 2nd ed., vol. 4, (1995), Noyes Publications, p. 114.*
Derwent abstract of JP 50088238, published Jul. 15, 1975.
Derwent abstract of DE 04244418, published Jul. 1, 1993.
Frei et al., "Activation of Fribroblast metabolism in a dermal and skin equivalent model: A Screening test for activity of peptides," International Journal of Cosmetic Scient., (1998) 20/3, pp. 159-173.
The SeaPlant Handbook, 2001.
Pribanich, et al. Low-Dose Tretinoin Does Not Improve Striae Distensae: A Double-Blind, Placebo-Controlled Study, Therapeutics for the Clinician, vol. 54, Aug. 1994, 121-124.
Shuster, "The Cause of Striae Distensae," Acta Dermatovener, (1979) 161-169.
Office Action issued Feb. 26, 2003, in U.S. Appl. No. 09/806,834, 8 pages.
Office Action issued Jul. 3, 2002, in U.S. Appl. No. 09/806,834, 9 pages.
Atwal, G.S.S., et al.; "Striae gravidarum in primiparae"; British Journal of Dermatology (2006); 155, pp. 965-969.
Salter, S., et al.; "Striae gravidarum"; Clinics in Dermatology (2006) 24, 97-100.
Cho, S., et al.; "Clinical features and risk factors for striae distensae in Korean adolescents"; (2006) European Academy of Dermatology and Venereology, 20, 1108-1113.
Marctunzi, MD., et al.; "Common Skin Conditions During Pregnancy"; www.aafp.org/afp, vol. 75, No. 2, Jan. 15, 2007.
Osman, et al.; "Risk Factors for the development of striae gravidarum"; Am J Obstet Gynecol, 2007, 196(1): 62.e1-62.e5.
Ghasemi, A., et al.; "Striae gravidarum: associated factors"; European Academy of Dermatology and Venereology, 21, 743-746 (2007).
Zheng, P. et al.; "Anatomy of striae"; British Journal of Dermatology; 112, 185-193 (1985).
Wilhelm, K. et al.;In Vivo Study on Age-Related Elastic Properties of Human Skin; In "Noninvasive Methods for the Quantification of Skin Functions: An Updated on Methodology and Clinical Applications". Frosch P. J. and Kigman A. M. Ed., Springer-Verlag, 1993: 190-203.
Watson, R. E. B. et al.; "Fibrillin microfibrils are reduced in skin exhibiting striae distensae"; British Journal of Dermatology; 138: 931-937 (1998).
Leveque, J. L. et al.; The Surface of the Skin—The Microrelief in Non Invasive Methods for the Quantification of Skin Functions: An updated on Methodology and Clinical Applications. Frosch P. J., Kligman A.M. Eds, Springer-Verlag, Berlin, New York, Paris 1993: 190-203.

\* cited by examiner

*Primary Examiner* — Gina C Justice
(74) *Attorney, Agent, or Firm* — Foley & Lardner LLP

(57) ABSTRACT

A method for reducing the formation of and/or treating skin stretchmarks is described. The method is characterized in that a composition is applied to the areas of skin liable to form or comprising stretchmarks, including skin of the thighs, abdomen, and/or breast. The applied composition includes a soya peptide, a tripeptide consisting of the amino acids glycine, histidine, and lysine, and/or mixtures of the soya peptide and tripeptide in a suitable application vehicle. The composition displays good skin tolerance.

24 Claims, No Drawings

COSMETIC METHOD FOR PREVENTING AND/OR TREATING SKIN STRETCHMARKS, AND USE IN DERMATOLOGY

CROSS-REFERENCE TO RELATED PATENT APPLICATIONS

This application is a continuation of U.S. application Ser. No. 09/806,834, filed Apr. 5, 2001, which is incorporated herein by reference in its entirety. U.S. application Ser. No. 09/806,834 is the National Stage of PCT/FR99/02375, filed Oct. 5, 1999, which claims priority to French application FR 98-12435, filed Oct. 5, 1998.

BACKGROUND

The present invention relates to a cosmetic method for preventing and/or treating skin stretchmarks, and to the use of a composition to prepare a dermatological medicinal product for preventing and/or treating stretchmarks.

Stretchmarks are visible marks on the skin resulting from the skin being stretched due to a gain in weight or mechanical stresses, which usually concern women, after puberty or a first pregnancy. About 50% of pregnant women develop stretchmarks, on the thighs, the abdomen and/or the breasts. Stretchmarks may also appear during physiological or pathological states such as obesity, tuberculosis and typhoid fever, and also during a relatively intensive dietary regime. The treatment of stretchmarks has been described, for example, in the article by P. Zheng et al., "Anatomy of striae", British Journal of Dermatology 112:185-193 (1985), in which it is especially reported that stretchmarks are scars resulting from an inflammation process which destroys elastic fibers.

Since then, many compounds have been proposed as active principles for treating stretchmarks, such as, for example, tretinoin (or all-trans-retinoic acid). According to the article by R. E. B. Watson et al., "Fibrillin microfibrils are reduced in skin exhibiting striae distensae", British Journal of Dermatology 138:931-937 (1998), it would appear that tretinoin has an anti-stretchmark action with a tendency toward essentially restoring the network of fibrillins, which are the main constituent of the microfibrils within elastic fibers, when compared with other constituents of the extracellular matrix.

However, although the active compounds of the prior art produce a stretchmark-regressing effect, it nevertheless remains that the results obtained are not entirely satisfactory, in particular given the well-known skin intolerance problem of tretinoin. There has thus hitherto been a real demand for the development of a product for efficiently preventing and/or treating, with acceptable skin tolerance, this complex and particularly unattractive problem of stretchmarks.

It has now been found, entirely surprisingly and unexpectedly, that the use of certain peptides makes it possible entirely significantly to prevent and/or treat skin stretchmarks, in a manner which is acceptable as regards skin tolerance.

SUMMARY

A subject of the present invention is thus a cosmetic method for preventing and/or treating skin stretchmarks, characterized in that a composition is applied to the areas of skin liable to form or comprising stretchmarks, this composition comprising, in a suitable vehicle, at least one anti-stretchmark agent chosen from the group consisting of soya peptides and tripeptides consisting of the amino acids glycine, histidine and lysine, and mixtures of these peptides.

According to the present invention, the expression "prevention of skin stretchmarks" means an action which prevents or at least reduces the formation of stretchmarks, i.e. their length, width and/or depth, in the context of a cosmetic or dermatological treatment, by applying the composition before and during an event known to cause the appearance of stretchmarks, such as pregnancy. According to the present invention, the expression "treatment of skin stretchmarks" means an action which visibly and measurably regresses, i.e. resorbs, in the context of a cosmetic or dermatological treatment, already-formed stretchmarks, i.e. their length, width and/or depth.

Thus, the composition used according to the invention may be applied to areas of skin liable to form stretchmarks, comprising stretchmarks in the process of being formed or even comprising already-formed stretchmarks.

The soya peptides in the composition used according to the present invention may be any peptide obtained by hydrolysis of proteins extracted from soya, under operating conditions known to those skilled in the art, in other words any soya protein hydrolysate. These soya peptides are preferably peptides which have also undergone a fermentation with a strain of microorganism. In general, a fermented soya peptide is obtained by placing a soya peptide in a fermenter in the presence of glucose, mineral salts and a given strain of microorganism, under controlled temperature, pH, oxygenation and time conditions. After the fermentation, the fermented soya peptide is obtained by conventional separating and filtering operations. This technique is especially used by the company Coletica which thus sells various fermented plant protein hydrolysates. The fermented or unfermented soya peptides in the composition used according to the present invention preferably have a molecular weight of between about 200 and about 20,000 daltons, as measured, for example, by electrophoresis.

One soya peptide which is particularly preferred for the composition used according to the invention is the fermented peptide known as "Phytokine®" as sold by the company Coletica.

This specific fermented soya peptide, with an average molecular weight of about 800 daltons, is obtained by fermenting a soya peptide with the *Lactobaccillus* microorganism strain, and its amino acid composition is as follows:

|       | Number of residues per 100 |
|-------|---------------------------|
| Hyp…  | 0.39                      |
| Asp…  | 12.64                     |
| Thr…  | 2.93                      |
| Ser…  | 4.29                      |
| Glu…  | 20.08                     |
| Pro…  | 7.31                      |
| Gly…  | 7.95                      |
| Ala…  | 7.76                      |
| Cys…  | ND*                       |
| Val…  | 5.59                      |
| Met…  | 0.96                      |
| Ile…  | 4.46                      |
| Leu…  | 7.42                      |
| Tyr…  | 1.38                      |
| Phe…  | 3.39                      |
| His…  | 2.12                      |
| Hyl…  | 0.09                      |
| Lys…  | 5.73                      |
| Trp…  | ND*                       |
| Arg…  | 5.53                      |
| βAla… | ND                        |

(*ND: not determined)

The expression "tripeptide consisting of the amino acids glycine, histidine and lysine" in particular means tripeptides of Gly-His-Lys sequence, the amino acids of which may be in D, L or DL form, which may be conjugated with a carboxylic acid such as acetic acid, in the form of a complex with a metal such as zinc or copper.

Among the tripeptides consisting of the amino acids glycine, histidine and lysine, it is preferred to use the tripeptide "Kollaren-CPP" whose INCI name is "tripeptide-1", as sold by the company Seporga. "Kollaren-CPP" is a tripeptide having the sequence Gly-His-Lys conjugated with acetic acid (acetate) in the form of a complex with zinc.

Thus, more particularly, the present invention relates to a cosmetic method for preventing and/or treating skin stretchmarks, characterized in that the anti-stretchmark agent is chosen from the group consisting of the soya peptide Phytokine® and the tripeptide Kollaren-CPP®, and mixtures of these peptides.

In the composition used according to the invention, the proportion of anti-stretchmark agent is between about 0.1% and about 10% by weight relative to the total weight of the composition.

DETAILED DESCRIPTION OF THE PREFERRED EMBODIMENTS

According to one preferred embodiment, the composition used according to the present invention also comprises at least one α-hydroxy acid, in combination with the anti-stretchmark agent. The reason for this is that it has been found, surprisingly, that the joint use of an α-hydroxy acid makes it possible at least to potentiate the activity of the anti-stretchmark agent, if not, in certain cases, to obtain a synergistic effect in preventing and/or treating stretchmarks.

The α-hydroxy acid used according to the invention may be any α-hydroxy acid which produces an exfoliation and/or moisturization effect on the skin, such as, for example, citric acid, pyruvic acid, glycolic acid or lactic acid.

One α-hydroxy acid which is particularly preferred for the composition used according to the invention is lactic acid.

The proportion of α-hydroxy acid is preferably between about 0.1% and about 20% by weight relative to the total weight of the composition.

Preferably, the composition used according to the invention comprises an anti-stretchmark agent chosen from the group consisting of the soya peptide Phytokine® and the tripeptide Kollaren-CPP®, and mixtures of these peptides, in combination with lactic acid as α-hydroxy acid. The reason for this is that it has been found that such a combination provides a particularly advantageous effect as regards the anti-stretchmark activity of the composition used according to the invention.

Finally, the composition used according to the invention also advantageously comprises a compound intended to adjust the pH of the composition according to the invention to a value of between about 2 and about 4, and preferably to a value of about 3.5, in particular to partially neutralize the α-hydroxy acid. In particular, arginine or an alkanolamine such as triethanolamine may be used.

According to one particularly preferred embodiment, the composition used according to the invention also comprises a substance-P and neuropeptide-Y (or NPY hereinbelow) inhibitor compound. This additional compound may be chosen from the substance-P and NPY inhibitor compounds known to those skilled in the art.

However, one substance-P and NPY inhibitor compound that is particularly preferred is a specific extract comprising an active peptide fraction, obtained from green algae (or chlorophycea) known as "*Enteromorpha compressa*" (or "Ao-nori" or "yellow green nori"), such as the product sold by the company Secma under the name "Enteline 2" (INCI name: "butylene glycol, glycerol, *Enteromorpha compressa* extract; CAS No. 92128-82-0).

Specifically, it has been observed that the use of this specific substance-P and neuropeptide-Y inhibitor compound makes it possible to obtain a particularly advantageous tolerance effect of the composition used according to the invention, in particular given the irritant effects of the α-hydroxy acid, in particular of lactic acid.

The proportion of substance-P and NPY inhibitor compound in the composition used according to the invention is preferably between about 0.1% and about 5% by weight relative to the total weight of the composition.

Preferably, the composition used according to the invention comprises an anti-stretchmark agent chosen from the group consisting of the soya peptide Phytokine® and the tripeptide Kollaren-CPP® and mixtures of these peptides, in combination with lactic acid and the Enteromorpha compressa extract.

The composition used according to the invention also comprises a suitable vehicle, which may be any vehicle among those known to a person skilled in the art, in order to obtain a cosmetic or dermatological composition which may be used according to the invention, in the form of a cream, a lotion, a gel, an ointment, etc., optionally in the form of an emulsion, also with components known to those skilled in the art for improving, modifying or stabilizing the composition from a cosmetic or dermatological point of view.

In particular, the composition used according to the invention may also comprise compounds contributing secondarily to the anti-stretchmark action, such as the extract of *Sophora japonica* which contributes toward controlling the vascularization of stretchmarks and thus their color, or alternatively silanol compounds such as methylsilanyl lactate, or trace elements based on copper and zinc which are constituents of dermal proteins, such as zinc gluconate and copper gluconate.

The operating conditions for preparing the composition used according to the invention form part of the general knowledge of a person skilled in the art.

Finally, a subject of the present invention is also the use of a composition as defined above to prepare a dermatological medicinal product for preventing and/or treating skin stretchmarks.

The examples which follow are intended to illustrate the present invention and should not in any way be interpreted as restricting its scope.

Example 1

Anti-stretchmark cream with a pH of 3.5.

|  | % |
|---|---|
| Cetyldimethicone, sold under the name "Albilwax 9801" by the company Goldschmitt | 2 |
| Octyl sebacate | 5 |
| Isononyl isononanoate | 7 |
| Mixture of glyceryl stearate, cetearyl alcohol, cetyl palmitate and cocoglycerides, sold under the name "Cutina CBS" by the company Sidobre Sinnova | 2.5 |
| Methyl paraben | 0.1 |
| Propyl paraben | 0.1 |
| Water | qs 100 |

-continued

|  | % |
|---|---|
| PEG 300 | 5 |
| Triethanolamine | 4.8 |
| Sepigel 305 ® (thickener sold by the company SEPPIC) | 5.5 |
| Phytokine ® | 2 |
| Lactic acid | 10 |
| Enteline 2 ® | 0.4 |
| Sophora japonica | 3 |
| Methylsilanyl lactate | 3 |
| Zinc gluconate | 0.2 |
| Copper gluconate | 0.2 |
| Fragrance | 0.35 |

Example 2

Anti-stretchmark cream with a pH of 3.5.

|  | % |
|---|---|
| Cetyldimethicone, sold under the name "Albilwax 9801" by the company Goldschmitt | 2 |
| Octyl sebacate | 5 |
| Isononyl isononanoate | 7 |
| Mixture of glyceryl stearate, cetearyl alcohol, cetyl palmitate and cocoglycerides, sold under the name "Cutina CBS" by the company Sidobre Sinnova | 2.5 |
| Methyl paraben | 0.1 |
| Propyl paraben | 0.1 |
| Water | qs 100 |
| PEG 300 | 5 |
| Triethanolamine | 4.8 |
| Sepigel 305 ® (thickener sold by the company SEPPIC) | 5.5 |
| Kollaren CPP ® | 2.5 |
| Lactic acid | 10 |
| Enteline 2 ® | 0.4 |
| Sophora japonica | 3 |
| Methylsilanyl lactate | 3 |
| Zinc gluconate | 0.2 |
| Copper gluconate | 0.2 |
| Fragrance | 0.35 |

Example 3

Clinical study to evaluate the effect of the compositions of Examples 1 and 2 on the regression of stretchmarks, on the basis of an instrumental evaluation combined with a clinical evaluation, after repeated applications to the skin, under the normal conditions of use, for 6 weeks, in 9 adult female volunteers.

1. Object of the Study

The object of the present study is to evaluate and compare the effect of the compositions of Examples 1 and 2 above on the "regression" of stretchmarks, by calorimetric measurements of stretchmarks on the skin of the thighs, combined with measurements of biomechanical parameters and with a clinical evaluation, after repeated applications to the skin for 6 weeks, under the normal conditions of use, in 9 adult female volunteers.

2. Relevance of the Test

Measurement of the viscoelastic parameters of the skin using a Cutometer® makes it possible to determine the effect of a product on the skin's biomechanical properties, after repeated applications. This apparatus measures the deformation of an area of skin subjected to a mechanical'suction stress, and its power of recovery (Wilhelm et al., 1993). Specifically, the viscoelastic properties of the skin are correlated with the notions of suppleness, elasticity and firmness of the tegurment.

Measurements using a Chromameter moreover make it possible to evaluate objectively the effect of a product on skin coloration, in an area with stretchmarks, compared with a control area (normal skin).

When combined with a clinical evaluation on the basis of scores by the Study Director, these instrumental techniques make it possible to evaluate the effect of a product on stretchmarks, in a panel of 9 adult female volunteers, after 6 weeks of twice-daily applications, under the normal conditions of use.

3. Volunteers 9 panel members were finally accepted by the Study Director on the basis of a clinical examination specific to the study, carried out just before the start of the trial. They all participated in the entire trial.

The analysis of the results was thus made on a panel of 9 adult female volunteers (or 8 for the colorimetric measurements) from 20 to 31 years old (average age: 26 years old), showing stretchmarks dating back less than 8 months.

4. Protocol 4.1 Initial Clinical and Instrumental Evaluations:
  4.1.1. Determination of the Viscoelastic Parameters:
  These parameters were evaluated on the skin of both thighs using a Cutometer™ (Courage+Khazaka, Germany), on two diametrically opposite areas delimited on the left and right thighs of each of the adult female volunteers specifically selected and recruited to carry out and objectivize this type of trial. These measurements were taken on an area showing stretchmarks, and also on an adjacent area without stretchmarks ("normal skin"), after marking the areas using a transparent plastic card bearing anatomical markers.
  4.1.2. Coloration Measurement
  The evaluation of the coloration of a stretchmark was carried out on the skin of both thighs and of an adjacent control area (free of stretchmarks) by analysis of the clarity variable "L*" and the chromaticity coordinates "a*" and "b*", using a CR 321 Chromameter (Minolta) fitted with a cone for colorimetric measurements on an area 3 mm in diameter.

These measurements were carried out after a rest period of about 20 minutes, in an air-conditioned room with an ambient temperature maintained at 22±2° C. and a relative humidity of 50±5%, by means of a microprocessor connected to temperature and humidity sensor-transmitters so as to achieve a stable equilibrium of water exchange between the skin of each panel member and the surrounding environment. The stability of these parameters was monitored and printed out continuously using a multipath recorder.
  4.1.3. Clinical Evaluation
  The following judgement criteria were evaluated, by the Deputy Study Director, on the basis of 9-point clinical scores (1 to 9), on both thighs, for each of the volunteers:
  size of the stretchmarks,
  color of the stretchmarks,
  relief of the stretchmarks.
  4.1.4. Photographs
  Color macrophotographs of an area of skin of each thigh were taken, using a Nikon F-801S camera fitted with a Nikon 105 MM macro objective lens, under lighting of "daylight" type (6500° K).

4.2. Determination of the Efficacy of the Products After Repeated Applications 4.2.1. Application Methods The products studied were applied twice a day for 6 consecutive weeks, under the normal conditions of use, by the volunteer herself at home, on the skin of both thighs (1 product for each thigh according to a randomization—binomial law).

In order to achieve the maximum standardization of the study conditions, the products studied were applied once a week, in the presence of the laboratory staff.

4.2.2. Effect on the Viscoelastic Properties of the Skin (Tonicity, Firmness, Suppleness, Elasticity)

The viscoelastic parameters of the skin of both thighs (areas with and without stretchmarks) marked out accurately relative to the first day of the test and according to the same principle, were determined after the sixth week of use of the products. This evaluation was carried out 16 to 24 hours after the last application of the products, by the laboratory staff, so as to specifically measure the variations in the elastic parameters of the skin tissue that are induced by the repeated uses.

4.2.3. Effect on the Coloration of the Skin

The skin coloration measurements were carried out using a Chromameter® after the 6 weeks of use, on the areas determined during the first day of the study and accurately marked out, according to the same principle (areas with and without stretchmarks).

4.2.4. Clinical Evaluations and Self-Evaluations

The evaluations of the skin of both thighs were carried out by the Study Director, on the basis of 6-35 point clinical scores, according to the same principle as that followed during the initial determination, after the 6 weeks of application.

4.2.5. Photographs

Color macrophotographs of the areas determined during the first day of the study and accurately marked out were taken, according to the same principle, after the 6 weeks of application.

4.3. Analysis and Interpretation of the Results 4.3.1. Biomechanical Parameters

The mean values of the viscoelastic parameters determined on D1 and D43 on the 2 thighs (areas with stretchmarks and areas without stretchmarks) were calculated by determining the arithmetic mean and the error obtained relative to the mean (S.E.M.) of the individual measurements taken on all of the panel members.

The initial values obtained on the right and left thighs (before the first application of the products) were compared by an analysis of variance (ANOVA, significance: $p<0.05$).

The values obtained after using the products for 6 weeks were compared with the initial values, determined before the first application, by the paired serial Student "t" test ("one-tail", significance: $p<0.05$), for each of the areas (right and left thighs, areas with and without stretchmarks).

The effects obtained on the right and left thighs (areas with and without stretchmarks) were compared by an analysis of variance (ANOVA, significance: $p<0.05$) and by the multiple comparison test ("L.S.D."), relating to the differences calculated between the values acquired after the 6 weeks of use and the initial values ($\Delta$D43-D1).

The mean variation percentages of the parameters evaluated during the trial were calculated for each area of skin, after the 6 weeks of application, relative to the initial value, starting with the mean values obtained for all of the panel members.

4.3.2. Colorimetric Measurements

The mean values of the colorimetric parameters, determined at each stage of the study, were calculated by determining the arithmetic mean and the error relative to the mean (S.E.M.) of the individual measurements taken on all of the panel members.

These determinations relate to the clarity variable "$L^*$", the chromaticity coordinates "$a^*$" and "$b^*$" and the Individual Typological Angle ITA°, calculated according to the following formula:

$$ITA°=[\text{arc tangent}(L^*-50)/b^*]180/3,14159$$

The initial values obtained on the right and left thighs (before the first application of the products) were compared by an analysis of variance (ANOVA, significance: $p<0.05$).

The values obtained after using the products for 6 weeks were compared with the initial values, determined before the first application, by the paired serial Student "t" test ("one-tail", significance: $p<0.05$), for each of the areas (right and left thighs, areas with and without stretchmarks).

The effects obtained on the right and left thighs (areas with and without stretchmarks) were compared by an analysis of variance (ANOVA, significance: $p<0.05$) and by the multiple comparison test ("L.S.D."), relating to the differences calculated between the values acquired after the 6 weeks of use and the initial values ($\Delta$D43-D1).

The mean variation percentages of the parameters evaluated during the trial were calculated for each area of skin, after the 6 weeks of application, relative to the initial value, from the mean values obtained for all of the panel members.

4.3.3. Clinical Scores

The mean values of the judgement criteria determined at each stage of the study on the basis of the clinical scores were calculated by determining the arithmetic mean and the standard deviation (Sd) of the individual data acquired for all of the panel members.

The values obtained, after applying the products, were compared with the values determined during the first day of the trial (initial evaluations) by the paired serial Wilcoxon test ("one-tail", significance: $p<0.05$), for each area treated.

The effect of the products was compared by a paired serial Wilcoxon test ("one-tail", significance: $p<0.05$) relating to the values obtained before and after repeated applications.

The mean variation percentages of each of the evaluation criteria were calculated relative to the initial data, starting with the mean values obtained for all of the volunteers.

5. Results and Conclusion 5.1. Cutometric Measurements

The statistical analysis previously demonstrated that the initial values of the biomechanical parameters were identical, firstly on each of the areas without stretchmarks, and secondly on each of the areas with stretchmarks. Statistically significant differences were moreover revealed between the areas with and without stretchmarks, reflecting a skin which is slacker and less elastic in the areas with stretchmarks.

5.1.1. Anti-stretchmark Cream of Example 1

The analysis of the results made it possible to reveal, after 6 weeks of application, relative to the initial measurement:

On the area without stretchmarks:
  a tendency toward decreasing the Uf (final elongation), by about 4% during the 1st and 3rd stress,
  a statistically significant decrease in Uv/Ue (degree of viscoelasticity determining the size of the viscous response relative to the elastic response), of about 14%.

On the area with stretchmarks:
  a tendency toward decreasing the Uf (final elongation), by about 2% during the 1st and 3rd stress, a stabilization of Ua/Uf (degree of recovery after stress)

a statistically significant decrease in Uv/Ue (degree of viscoelasticity determining the size of the viscous response relative to the elastic response) of about −17%.

A significant improvement in the firmness and tonicity components is thus found, on the area with stretchmarks.

5.1.2. Anti-stretchmark Cream of Example 2

The analysis of the results made it possible to reveal, after 6 weeks of application, relative to the initial measurement:

On the area without stretchmarks:
  a statistically significant decrease in Uf (final elongation), of about 6% during the 1 st and 3rd stress,
  a stabilization in Ua/Uf (degree of recovery after stress)
  a stabilization of Uv/Ue (degree of viscoelasticity).

On the area with stretchmarks:
  a tendency toward decreasing the Uf (final elongation), by about 2% during the 1 st stress,
  a stabilization of Ua/Uf (degree of recovery after stress),
  a tendency toward decreasing the Uv/Ue (degree of viscoelasticity), by about 9%.

A marked tendency (non-significant for the 9 panel members) toward improving the tonicity and firmness components of the skin in the area with stretchmarks is thus found.

5.2. Colorimetric Measurements

The statistical analysis previously demonstrated that the initial values of the calorimetric parameters were identical, firstly on each of the areas without stretchmarks, and secondly on each of the areas with stretchmarks. It should be noted that the skin of the areas with stretchmarks (before and after using the products for 6 weeks) was paler than that of the areas without stretchmarks (higher clarity variable L* and higher I.T.A.°).

No favorable and statistically significant improvement in the colorimetric parameters was recorded, after using each of the products, irrespective of the areas (with and without stretchmarks).

5.3. Clinical Evaluations by the Study Director

The analysis of the results made it possible to reveal a statistically significant improvement in the following criteria, with the exception of the length of the stretchmarks. A significant difference was moreover noted between the two products studied for this criterion, reflecting a greater regression of stretchmarks on the area treated with the anti-stretchmark cream of Example 2.

TABLE 1

| | Anti-Stretchmark Cream | |
|---|---|---|
| | Example 1 | Example 2 |
| Width of the Stretchmarks (thin → broad) | −17%* | −14% |
| Length of the Stretchmarks (short → long) | −8% | −14%• |
| Color of the Stretchmarks (abnormal → normal) | −18% | −26%* |
| | (tendency close to the significant level) | |
| Relief of the Stretchmarks (hollow/puffy → normal) | −26%* | −16%* |

*statistically significant value at time 6 weeks, relative to the initial evaluation
•statistically significant decrease compared with the anti-stretchmark cream of Example 1 (Wilcoxon test, "one-tail").

5.4. Tolerance of the Cosmetic Product Assessed by the Volunteer

Skin sensations experienced:
  none: 100%
Best-tolerated product:
  no difference: 100%

No pathological irritation reaction significant 20 of a skin intolerance was noted. The 9 volunteers also indicated that they did not observe any irritation and/or discomfort sensations during the trial.

6. Conclusion

In conclusion, the anti-stretchmark creams of Examples 1 and 2, which differ from each other only in the anti-stretchmark active agent used, applied for 6 consecutive weeks under the normal conditions of use, to 9 adult female volunteers, made it possible to obtain a regression of stretchmarks, demonstrated by instrumental methods and on the basis of clinical scores.

This effect is reflected:
  for the cream of Example 1 (use of "Phytokine®"):
    by a statistically significant improvement in the tonicity and firmness components of the skin;
    by statistically significant regression of the width of the stretchmarks (−17%) and of their relief (−26%), with a non-significant tendency on their color (−18%);
  for the cream of Example 2 (use of "Kollaren-CPP®"):
    by a marked, non-significant tendency toward improving the tonicity and firmness components of the skin;
    by a statistically significant decrease in the length of the stretchmarks, compared with the cream of Example 1;
    by a statistically significant improvement in the color (−26%) and the relief (−16%) of the stretchmarks.

BIBLIOGRAPHIC REFERENCES

Leveque J. L., Corcuff P. The Surface of the Skin—The Microrelief In Non Invasive Methods for the Quantification of Skin Functions: An Update on Methodology and Clinical Applications. Frosch P. J., Kligman A. M. Eds, Springer-Verlag, Berlin, New York, Paris 1993; 3-24.

Wilhelm K. P., Cua A. B. and Maibach H. I. In vivo study on age-related elastic properties of Human skin. In "Noninvasive Methods for the Quantification of Skin. Functions: An Update on Methodology and Clinical Applications". Frosch P. J. and Kigman A. M. Ed., Springer-Verlag, 1993: 190-203.

The invention claimed is:

1. A method for reducing the formation of and/or treating skin stretchmarks in a person, comprising
applying to at least one area of skin comprising one or more stretchmarks a composition comprising, in a suitable vehicle, at least one soya peptide.

2. The method according to claim 1, wherein the soya peptide is obtained by hydrolyzing a protein extracted from soya.

3. The method according to claim 2, wherein the soya peptide is obtained by fermenting the peptide.

4. The method according to claim 3, wherein the soya peptide is obtained by fermenting the peptide with a strain of *Lactobaccillus*.

5. The method according to claim 3, wherein the soya peptide has a molecular weight of about 200 daltons to about 20,000 daltons.

6. The method according to claim 3, wherein the soya peptide has a molecular weight of about 800 daltons.

7. The method according to claim 1, wherein the soya peptide is between about 0.1% and about 10% by weight relative to the total weight of the composition.

8. The method according to claim 1, wherein the composition further comprises at least one α-hydroxyacid.

9. The method according to claim 8, wherein the proportion of α-hydroxyacid is between 0.1% and about 20% by weight relative to the total weight of the composition.

10. The method according to claim 8, wherein the α-hydroxyacid is lactic acid.

11. The method according to claim 1, wherein the composition further comprises a compound for adjusting the pH to a value of between about 2 and about 4.

12. A method for reducing the formation of and/or treating skin stretchmarks in a person, comprising applying to at least one area of skin comprising one or more stretchmarks a composition comprising, in a suitable vehicle, at least one tripeptide consisting essentially of the amino residues glycine, histidine, and lysine.

13. A method for reducing the formation of and/or treating skin stretchmarks in a person, comprising applying to at least one area of skin comprising one or more stretchmarks and/or an at least one area liable to form stretchmarks, a composition comprising, in a suitable vehicle, at least one tripeptide having the sequence Gly-His-Lys, and the tripeptide is conjugated with acetic acid or acetate in the form of a complex with zinc.

14. The method according to claim 13, wherein the tripeptide is between about 0.1% and about 10% by weight relative to the total weight of the composition.

15. The method according to claim 13, wherein the composition further comprises at least one α-hydroxyacid.

16. The method according to claim 15, wherein the proportion of α-hydroxyacid is between 0.1% and about 20% by weight relative to the total weight of the composition.

17. The method according to claim 13, wherein the composition further comprises lactic acid.

18. The method according to claim 13, wherein the composition further comprises a compound for adjusting the pH to a value of between about 2 and about 4.

19. A method for reducing the formation of and/or treating skin stretchmarks in a person, comprising applying a composition to areas of skin liable to form stretchmarks or having stretchmarks, the composition comprising, in a suitable vehicle, a mixture of at least one soya peptide and at least one tripeptide selected from tripeptides wherein the tripeptide has the sequence Gly-His-Lys, and the tripeptide is conjugated with acetic acid or acetate in the form of a complex with zinc.

20. A method for reducing the formation of and/or treating skin stretchmarks in a person, comprising applying to at least one area of skin comprising one or more stretchmarks and/or an at least one area liable to form stretchmarks, a composition comprising, in a suitable vehicle, at least one soya peptide and at least one tripeptide consisting essentially of the amino residues glycine, histidine, and lysine.

21. The method of claim 1, wherein the one or more stretchmarks are a result selected from puberty, pregnancy, a gain in weight and mechanical stress.

22. The method of claim 1, wherein the at least one area of skin is selected from skin of thighs, skin of abdomen, skin of breast and combinations thereof.

23. The method of claim 12, wherein the one or more stretchmarks are a result selected from puberty, pregnancy, a gain in weight and mechanical stress.

24. The method of claim 12, wherein the at least one area of skin is selected from skin of thighs, skin of abdomen, skin of breast and combinations thereof.

\* \* \* \* \*